United States Patent [19]
Tazawa et al.

[11] Patent Number: 4,816,748
[45] Date of Patent: Mar. 28, 1989

[54] ELECTRONIC THERMOHYGROMETER WITH SQUARE-WAVE PULSE SIGNAL GENERATOR

[75] Inventors: Isao Tazawa, Nagano; Norihiro Kiuchi, Tokyo; Hideo Segawa, Saitama; Chikara Tominaga, Tokyo; Kenji Murakami, Nagano, all of Japan

[73] Assignees: Nippon Mining Co., Ltd.; Soar Corporation, both of Tokyo, Japan

[21] Appl. No.: 79,735

[22] Filed: Jul. 30, 1987

[30] Foreign Application Priority Data

| Aug. 28, 1986 | [JP] | Japan | 61-200180 |
| Aug. 28, 1986 | [JP] | Japan | 61-200181 |
| Sep. 18, 1986 | [JP] | Japan | 61-218240 |
| Dec. 12, 1986 | [JP] | Japan | 61-297220 |
| Dec. 15, 1986 | [JP] | Japan | 61-298482 |

[51] Int. Cl.$^4$ .................. G01W 1/02; G01R 27/02; G01K 7/16; G01N 27/04
[52] U.S. Cl. .................. 324/65 R; 73/336.5; 331/65; 331/66; 340/602; 374/183
[58] Field of Search .................. 324/65 R; 73/336.5; 340/602; 331/65, 66; 374/183-185

[56] References Cited
U.S. PATENT DOCUMENTS

| 3,670,243 | 6/1972 | Fougere et al. | 324/65 R X |
| 4,104,619 | 8/1978 | Hesler | 331/65 X |
| 4,129,833 | 12/1978 | Shibata | 324/65 R X |
| 4,150,573 | 4/1979 | Iinuma et al. | 331/66 X |
| 4,662,220 | 5/1987 | Laue | 73/336.5 |

FOREIGN PATENT DOCUMENTS

| 0046305 | 4/1981 | Japan | 331/65 |
| 0020845 | 2/1984 | Japan | 324/65 R |
| 0134653 | 6/1986 | Japan | 324/65 R |

*Primary Examiner*—Gerard R. Strecker
*Attorney, Agent, or Firm*—Seidel, Gonda, Lavorgna & Monaco

[57] ABSTRACT

An electronic hygrometer and an electronic thermohygrometer both comprising oscillation means and digital operation processing means. The oscillation means of the hygrometer includes a square-wave pulse signal generator, a humidity sensor connected to the generator and which exhibits characteristics variable with the humidity change of the atmosphere, and a passive element connected to the generator and which forms a time constant circuit with the characteristics of the humidity sensor, the passive element being of a type different from the humidity sensor. The oscillation means produces square-wave pulse signals corresponding to changes in the characteristics of the sensor. The digital operation processing means of the hygrometer counts the frequency of the square-wave pulse signals output from the oscillation means and determines the humidity of the atmosphere on the basis of the counted value. The thermohygrometer further comprises a reference resistance element connected in parallel with the humidity sensor, a temperature sensor connected in parallel with the humidity sensor and the resistance element and which exhibits electric resistance variable with the temperature change of the atmosphere, and switching means which open and close the circuits of the humidity sensor, resistance element, and temperature sensor.

3 Claims, 11 Drawing Sheets

ELECTRONIC THERMOHYGROMETER WITH SQUARE-WAVE PULSE SIGNAL GENERATOR

BACKGROUND OF THE INVENTION

This invention relates generally to an electronic hygrometer and an electronic thermometer-hygrometer (hereinafter referred to as "electronic thermohygrometer"). More specifically, the invention relates to a digital electronic hygrometer including a humidity sensor which detects the change in humidity of the atmosphere and produces an electric signal corresponding to the detected humidity change, and relates also to a digital electronic thermohygrometer including, in addition to the humidity sensor, a temperature sensor whose electric resistance or electrostatic capacity is variable with the temperature change of the atmosphere.

As is well known, digital electronic hygrometers of this type are comprised of a sensor unit including a humidity sensor which detects the humidity change of the atmosphere and produces an electric signal corresponding to the detected humidity change; and a signal processing unit connected to the sensor unit and consisting essentially of an amplifier, analog-to-digital converter (hereinafter referred to as "a-d converter"), and digital electronic circuit controls such as a microcomputer and microprocessor (the controls being hereinafter referred to as "microcomputer"). In the digital electronic hygrometer, an analog voltage signal produced by and output from the humidity sensor of the sensor unit is input to the signal processing unit, where the signal is amplified by the amplifier and is converted into a digital signal through the a-d converter. The digital signal is then led to the microcomputer which calculates the humidity value of the atmosphere on the basis of the digital signal.

As is obvious from the foregoing, the conventional digital electronic hygrometer requires that the amplifier for amplifying an analog signal output from the humidity sensor and the a-c converter for converting the analog signal from the amplifier into a digital one be connected in between the humidity sensor and the microcomputer, so that the microcomputer can calculate the humidity of the atmosphere on the basis of the analog voltage signal produced by the humidity sensor correspondingly to the atmospheric humidity change. The requirement has made it difficult to contain the whole circuitry inclusive of the microcomputer, amplifier, a-d converter, and the like in a single LSI chip, with consequent limitations on miniaturization, power saving, and cost reduction.

In view of these, we have made an extensive study and have found that the number of circuit components of the digital electronic hygrometer can be reduced and the whole circuitry built up as a single-chip LSI by omitting the relatively expensive a-d converter and using instead other technical means having the function of the converter.

It has also been found possible to build, in a single-chip LSI, the electronic thermohygrometer that can measure both the humidity and temperature by incorporating a thermistor or other element as a temperature sensor in the circuit of the digital electronic hygrometer.

The present invention is based upon these novel discoveries.

SUMMARY OF THE INVENTION

This invention, contrived in view of the aforedescribed circumstances, has for an object to provide an electronic hygrometer which dispenses with the relatively expensive a-d converter to reduce the number of circuit components and has the whole circuitry contained in a single-chip LSI, making it possible to reduce the size, power consumption, and manufacturing cost.

Another object is to provide an electronic thermohygrometer which eliminates the relatively expensive a-d converter to reduce the number of circuit components, and uses a circuitry built up within a single-chip LSI, thus reducing the size, power consumption, and cost.

The above objects are achieved by an electronic hygrometer and an electronic thermohygrometer according to the invention. In brief, the invention in one aspect to concerned with an electronic hygrometer which comprises: oscillation means including a square-wave pulse signal generator, a humidity sensor connected to the square-wave pulse signal generator and which exhibits characteristics variable with the humidity change of the atmosphere, and a passive element connected to the square-wave pulse signal generator and which forms a time constant circuit with characteristics of the humidity sensor, said passive element being of a type different from the humidity sensor, said oscillation means producing square-wave pulse signals corresponding to changes in the characteristics of the humidity sensor; and digital operation processing means which counts the frequency of the square-wave pulse signals output from the oscillation means and finds the humidity of the atmosphere based upon the counted value.

The invention in a second aspect is concerned with an electronic thermohygrometer which comprises: oscillating means including a square-wave pulse signal generator, a humidity sensor connected to the square-wave pulse signal generator and which exhibits electric resistance variable with the humidity change of the atmosphere, a reference resistance element connected in parallel with the humidity sensor, a temperature sensor connected in parallel with the humidity sensor and the reference resistance element and which exhibits electric resistance variable with the temperature change of the atmosphere, first switching means which opens and closes the circuit of the humidity sensor, second switching means which opens and closes the circuit of the reference resistance element, third switching means which opens and closes the circuit of the temperature sensor, and a capacity element connected to the square-wave pulse signal generator and which forms a CR time constant circuit with the electric resistance of the humidity sensor, with the resistance of the reference resistance element, or with the electric resistance of the temperature sensor, said oscillation means producing square-wave pulse signals corresponding to changes in electric resistance of the humidity sensor when the first switching means only is closed, or signals corresponding to the resistance of the reference resistance element when the second switching means only is closed, or signals corresponding to changes in electric resistance of the temperature sensor when the third switching means only is closed; and digital operation processing means which calculates the ratio of the oscillation frequency of square-wave pulse signals output from the oscillation means when the first switching means only is closed to the oscillation frequency of square-wave pulse signals from the oscillation means when the second switching means only is closed, said ratio corresponding to the ratio of the electric resistance of the humidity sensor to the resistance of the reference resistance element, or which calculates the ratio of the oscillation frequency of square-wave pulse signals output from the oscillation means when the third switching means only is closed to the oscillation frequency of square-wave pulse signals from the oscillation means when the second switching means only is closed, said ratio corresponding to the ratio of the electric resistance of the temperature sensor to the resistance of the reference resistance element, and which finds the humidity or temperature of the atmosphere on the basis of the counted result.

DESCRIPTION OF THE PREFERRED EMBODIMENTS

Figure 1:
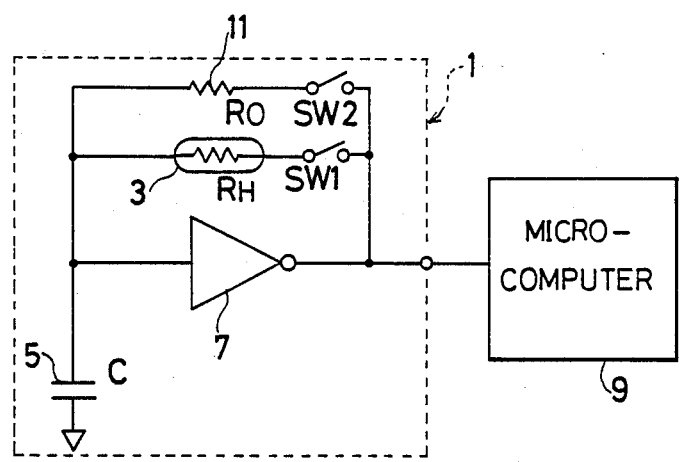
FIG. 1 is a circuit diagram of a first embodiment of the electronic hygrometer of the invention.

The invention will now be described in connection with the embodiments thereof shown in the drawings.

FIG. 1 illustrates an electronic hydrometer as a first embodiment of this invention. As is obvious from FIG. 1, the first embodiment comprises oscillation means, i.e., a square-wave pulse generator 1, and digital operation processing means, i.e., a microcomputer 9 which receives output signals from the square-wave pulse generator 1. The square-wave pulse generator 1 consists of a square-wave pulse signal generator, i.e., an inverter element 7 which produces square-wave pulse signals that serve as logic level signals; a humidity sensor 3 and a switch SW1 connected in series with the humidity sensor 3 to open and close the circuit of the humidity sensor 3 for constituting a first feedback circuit of the inverter element 7; a reference resistance element RO11 and a switch SW2 connected in series with the reference resistance element RO11 to open and close the circuit of the reference resistance element RO11; and a capacitor element (hereinafter referred to as "capacitor") 5 that constitutes a CR time constant or CR oscillation circuit with the electric resistance of the humidity sensor or with the electric resistance of the reference resistance element RO11.

Figure 2:
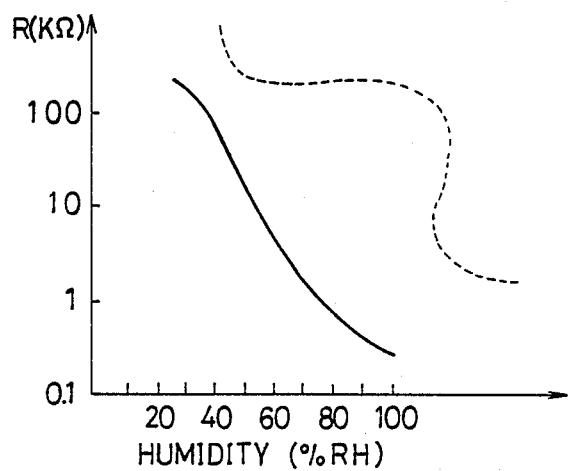
FIG. 2 is a graph showing the humidity-electric resistance characteristics of a variable resistance-type humidity sensor employed in the electronic hygrometer and electronic thermohygrometer according to the invention.

As is well known, the humidity sensor 3 exhibits electric resistance variable with the humidity change of the atmosphere. In this embodiment of the invention, the humidity sensor 3 is made of a ceramic humidity-sensitive material which is a solid solution, for example, of zirconia ($ZrO_2$) and at least one selected from yttria ($Y_2O_3$), calcia (CaO), and magnesia (MgO). Its humidity-electric resistance characteristics, as represented by a solid line in FIG. 2, are such that the electric resistance changes range from 170 kΩ to 300 Ω for the humidity changes from 30 to 95%. Details of the ceramic humidity sensor 3 will be described later. As the electric resistance of the ceramic humidity sensor 3 changes with the humidity of the atmosphere, with the switch SW1 closed and switch SW2 open, and accordingly the oscillation frequency of the CR oscillation circuit formed between the electric resistance of the ceramic humidity sensor 3 and the capacitor 5 undergoes a change, the inverter element 7 produces square-wave pulse signals of a frequency corresponding to the oscillation frequency.

The inverter element 7 is also designed so that, when the switch SW2 is closed and the switch SW1 is open, it produces square-wave pulse signals of a frequency corresponding to the oscillation frequency of the CR oscillation circuit constituted by the reference resistance element RO11 and the capacitor 5. The square-wave pulse signals produced by the inverter element 7 and processing of the signals will be described later.

In this embodiment, the inverter element 7 uses a C-MOS Schmidt inverter to reduce the manufacturing cost and electric power consumption. The inverter further makes it possible to obtain stably square-wave pulse signals even at frequencies of the order, e.g., of 100 kHz.

The microcomputer 9 comprises a CPU which performs arithmetic and logic operations, a counter for counting the square-wave pulse signals output from the square-wave pulse generator 1, a memory containing a control program and for storing necessary data, input and output ports, etc. The memory of the microcomputer 9 will store the data of humidity-electric resistance characteristics of the ceramic humidity sensor 3 represented by a solid line in FIG. 2, temperature compensation data of the humidity sensor 3, and an equation representing the relationship between the oscillation frequency f of square-wave pulse signals output from the generator 1 and the electric resistance R of the humidity sensor 3 shown in FIG. 1, i.e., $$f = 1 / \left\{ k \cdot R \cdot C \cdot \ln\left(\frac{VO - VTL}{VO - VTH}\right) \right\} \quad (1)$$

where
- VO = output voltage of the square-wave pulse generator 1,
- VTH = high-level threshold voltage of the inverter element 7 (C-MOS Schmidt inverter)
- VTL = low-level threshold voltage of the inverter element 7 (C-MOS Schmidt inverter).
- k = constant.

The CPU of the microcomputer 9 calculates a ratio rf = fH/fO of an oscillation frequency fH of square-wave pulse signals output from the square-wave pulse generator 1 when the switch SW1 only is closed to an oscillation frequency fO of square-wave pulse signals output from the square-wave pulse generator 1 when the switch SW2 only is closed, the ratio rf = fH/fO corresponding to a ratio RO/RH of the electric resistance RH of the ceramic humidity sensor 3 to the resistance RO of the reference resistance element RO11. From the relationship rf = fH/fO = RO/RH, the CPU finds a value RH as RH = RO/rf and then finds the humidity of the atmosphere from the RH value and the data represented by the solid line in FIG. 2. The square-wave pulse generator 1 is constructed as described above for the reasons to be explained below. We have experimented with the square-wave pulse generator 1 of the most basic structure consisting of the inverter element 7, the ceramic humidity sensor 3 connected to the feedback circuit of the inverter element 7, and the capacitor 5 connected to the input of the inverter element 7. It has now been found, as a result, that the oscillation frequency f of the generator 1 is influenced to some extent by the temperature characteristics and variations in the values of capacity C of the capacitor 5, high-level threshold voltage VTH of the inverter element 7, low-level threshold voltage VTL of the element 7, output voltage VO of the generator 1, and constant k. We therefore connected the reference resistance element RO11 in parallel with the ceramic humidity sensor 3 and provided the switches SW1 and SW2 in such a manner that when either was closed the other was open. The oscillation frequency fH $$\left( fH = 1 / \left\{ k \cdot RH \cdot C \cdot \ln - \left(\frac{VO - VTL}{VO - VTH}\right) \right\} \right)$$

when the switch SW1 only was closed and the oscillation frequency fO $$\left( fO = 1 / \left\{ k \cdot RO \cdot C \cdot \ln\left(\frac{VO - VTL}{VO - VTH}\right) \right\} \right)$$

when the switch SW2 only was closed, were counted by the microcomputer 9. Then, the ratio of fH to fO were found to erase VTH, VTL, VO, k and C, and the oscillation frequency f was determined from the value RO/RH only, whereby more accurate humidity measurement data were obtained. The resistance of the reference resistance element RO11 varies almost negligibly with changes in temperature as compared with the variations in the characteristic values of VTH, VTL, VO, C, and k. By finding the value rf, i.e., fH/fO while eliminating the values VTH, VTL, VO, C, and k, therefore, it is possible to determine the ratio rf solely on the basis of the electric resistance RH of the humidity sensor 3, thus achieving the humidity measurement with greater precision. The switches SW1 and SW2 are usually comprised of analog switches or three-state buffers.

Figure 3:
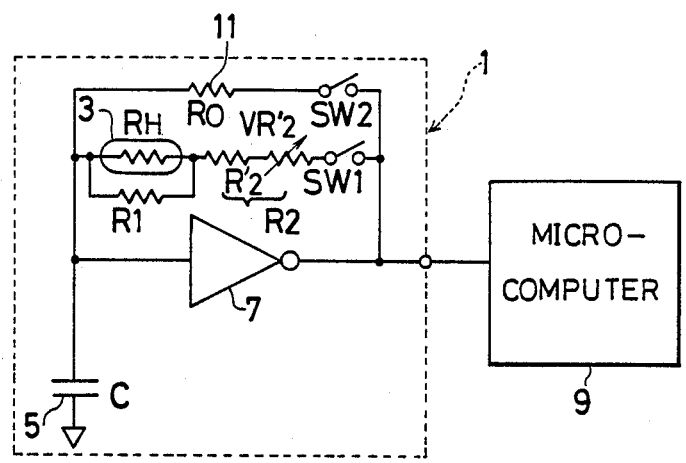
FIG. 3 is a circuit diagram of a second embodiment of the electronic hygrometer of the invention.

FIG. 3 illustrates an electronic hygrometer as a second embodiment of the invention. As is clear from FIG. 3, the second embodiment of the electronic hygrometer comprises the square-wave pulse generator 1 of the same circuit structure as shown in FIG. 1 but the first feedback circuit includes a first protective resistance element, or protective resistance element R1 connected in parallel with the ceramic humidity sensor 3, said ceramic humidity 3 and said protective resistance element R1 forming a resultant resistance, a second protective resistance element, or protective resistance element R2 consisting of a fixed resistance element R2 and a variable resistance element VR'2 connected in series, connected to said resultant resistance in series, and a switch SW1 connected in series with said protective resistance element R2. The square-wave pulse generator 1 is constructed as described above for the following reasons. The electric resistance of the ceramic himidity sensor 3 that varies with the humidity change of the atmosphere is confined so as not to be above or below a predetermined range. This prevents the square-wave pulse generator 1 from producing square=wave pulse signals of a frequency higher or lower than the oscillation frequency data in a given range stored in the memory of the microcomputer 9. If the square-wave pulse generator 1 produces square-wave pulse signals of a frequency outside the given range of oscillation frequency, the CPU causes a display unit (not shown) to indicate the overflow or underflow. In experiment with the square-wave pulse generator 1 constructed as above, the resistance of the protective resistance element R1 was set to 190 kΩ, the resistance of the protective resistance element R2, i.e., the sum of resistance R'2+VR'2 of the fixed resistance element R'2 and the variable resistance element VR'2 to be 10 kΩ, the resistance of the reference resistance element RO11 to be 200 kΩ, and the capacitance of the capacitor Cr to be 0.0022 μf. The humidity sensor 3 that exhibited the humidity = electric resistance characteristics as shown in Table 1 below was used to find by calculation the ratio rf (= fH/fO) and the humidity-rf characteristics data of the ceramic humidity sensor 3 that showed the particular rf ratio-humidity relationship, the data being as shown in FIG. 4.

TABLE 1

| Humidity (%) | RH (kΩ) |
| --- | --- |
| 30% | 166.95 kΩ |
| 40 | 78.55 |
| 50 | 20.21 |
| 60 | 5.13 |
| 80 | 0.99 |
| 90 | 0.56 |
| 95 | 0.32 |

Figure 4:
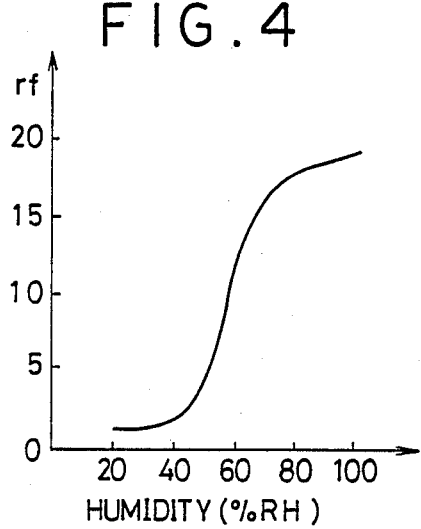
FIG. 4 is a graph showing the humidity-rf characteristics of the humidity sensor used in the electronic hygrometer of FIG. 3.

We also experimented with the square-wave pulse generator 1 of the structure mentioned above to obtain experimental data close to the calculated humidity-rf characteristics shown in FIG. 4. In finding the data, the ratio of rf was set to be 1 to about 20 for the convenience of counting.

The ceramic humidity sensor used in the electronic hygrometer and in the electronic thermohygrometer of the invention to be dealt with later, and the method of manufacturing the ceramic humidity sensor are as typically described below.

The ceramic humidity sensor to be employed in accordance with the invention may be of a type in which a pair of electrodes are formed on the opposing faces of sintered ceramic pieces. Preferably, it is made as a thick film type having a humidity=sensitive film formed on a substrate. The structure of the thick film-type humidity sensor is as shown, e.g., in FIG. 5, wherein an electrode layer 103 is formed on one side or both sides of a substrate 101, and a humidity-sensitive film layer 105 (shown as partly broken away) is formed on the electrode layer. The substrate 101 is made of a ceramic such as $Al_2O_3$, $SiO_2$, or $ZeO_2$. The electrode layer is formed on the substrate 101, e.g., with gold, silver, platinum, or ruthenium by the screen printing, vacuum deposition, or photoetching method.

Figure 5:
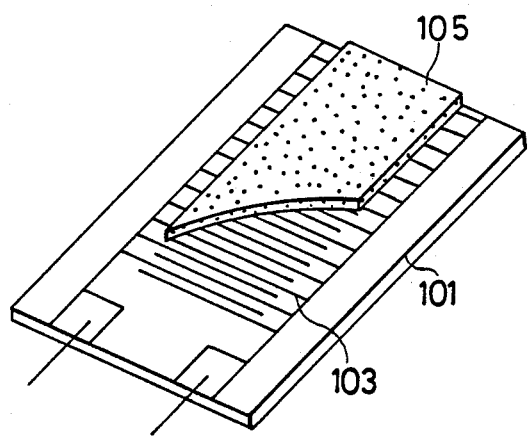
FIG. 5 is a schematic view of the structure of a ceramic humidity sensor used in the electronic hygrometer and electronic thermohygrometer of the invention.

In recent years varied fine processing techniques have come into use to fabricate printed circuit boards for electronic circuits, and they can be utilized in drawing fine electrode patterns. For instance, sputtering is a useful means. The electrode pattern preferably consists of a pair of comb-shaped electrodes, with the sets of comb teeth staggeredly engaged as shown in FIG. 5. The resistance decreases proportionally with the decrease in distance between the comb teeth sets, and accordingly the sensitivity of the humidity sensor improves. Good results are obtained when the comb teeth distance is from 0.05 to 0.20 mm.

Comb teeth-shaped gold electrodes are particularly effective in decreasing the resistance of the humidity sensor. Gold electrodes formed by the screen printing method as desirable. Where the sensor is to be small in size, gold electrodes formed by vacuum deposition is preferred.

A step for preparing a paste for the humidity-sensitive material will now be described.

For the electronic hygrometer and for the below-described electronic thermohygrometer of the invention, the ceramic humidity sensitive material is formed of a stabilized $ZrO_2$ powder. The stabilized $ZrO_2$ comprises $ZrO_2$ and at least one selected from $Y_2O_3$, CaO, and MgO in the form of a solid solution, with a composition falling in the solid-solution region on the $ZrO_2$ side in the phase diagram. A $ZrO_2$-$Y_2O_3$ system is preferred. $Y_2O_3$ may be added in an amount 10 to 60% by weight. The power formed of $ZrO_2$-$Y_2O_3$ solid solution is a homogeneously mixed powder obtained by the coprecipitation reaction of a mixture of $ZrOCl_2$ and $YCl_3$ at a predetermined ratio with an alkali such as $NH_3$ (ammonia), so that $Y_2O_3$ is contained in $ZrO_2$ in the form of a solid solution in the state of raw material powders. The solid=solution powder may be prepared by hydrolysis, alkoxide process, or melting, besides the coprecipitation. After prebaking at 600° to 800° C., the mixture is baked at 900° to 1100° C., and is ground by a ball mill to −625 mesh as a starting powder. The powder is then pretreated so that at least one selected from KOH, $K_2O$, and $K_2CO_3$ is added by a reaction in accordance with the invention. Treatment with KOH is preferred, in which case the powder is immersed in a solution containing KOH at a concentration of 5 to 20% by weight for 1 to 20 minutes with stirring. In this way the powder containing 1 to 10% by weight KOH is obtained.

The powder pretreated for impregnation with KOH or the like is then filtered and dried, and is primarily baked at 800° to 1150° C.

It is desirable to add 1 to 15 mol% of $Li_2CO_3$ to the powder at this stage to improve the stability, precision, and sensitivity of the resulting humidity sensor. The amount must be greater than 1 mol% so that the addition may be effective. If the amount exceeds 5 mol%, however, the resistance increases objectionably.

The mixture is then subjected to secondary baking at 700° to 900° C., and is ground again.

The resulting powder is thoroughly kneaded in admixture with a suitable resin coating material and the viscosity is adjusted with ethyl acetate or the like to prepare a paste humidity-sensitive material.

The thus obtained humidity-sensitive past is applied to the electrode layer by screen printing so that the final film thickness is from 5 to 200 μm, preferably from 20 to 50 μm.

After drying, the paste is baked at 500° to 870° C., typically at 700° to 870° C. A baking time of 5 to 90 minutes, usually 8 to 20 minutes, is sufficient for baking the ceramic particles into a skeletal structure of humidity-sensitive film and impart structural rigidity.

Following the formation of the humidity-sensitive film, the steps of assembling the element are carried out including soldering, aging, casing, and marking, to obtain a complete element. The aging is effected at 50° to 90° C., preferably 60° to 85° C., to obtain a stabilized element that deteriorates little under the service conditions to be encountered.

The completed humidity sensor is exposed to the atmosphere in varied service environments to detect the water vapor content. Its performance deteriorates upon deposition on its sensing part of liquid water, carbon black, exhaust emissions, cement powder, pollen and other dust and dirt suspended in the atmosphere. Deposition of water is particularly detrimental.

In order to keep off water, dust and dirt from the sensing part, it is desirable to accommodate the humidity sensor in a casing having a window fitted with a filter film in the portion facing the humidity sensing part.

The filter film must effectively prevent harmful substances such as water, dust and dirt from reaching the sensing part, while being responsive enough to transmit any wet atmosphere quickly to the sensing part. As filter films that satisfy these requirements, polymeric filter films such as of fluorocarbon resin and silicone resin have been introduced. The present applicant has already confirmed that a chlorine-containing polymer film that meets the following requirements, typically a chlorinated ethylene film, exhibits excellent properties.

(1) Porosity 35–85%
(2) Pore diameter 0.01–3 μm
(3) Thickness 20–200 μm

On a single piece of substrate are usually printed, e.g., 24 elements. If the treatment with KOH is effected after the humidity-sensitive film has been formed, the conductor pads for mounting lead pins too are treated likewise to impair the solderability in soldering at a later stage. According to the method of the invention in which the humidity-sensitive powder is KOH-treated before the baking, there occurs no such deterioration of solderability.

The humidity sensor using the ceramic humidity-sensitive material exhibits humidity-electric resistance characteristics as represented by a solid line in FIG. 2. It shows marked improvements in characteristics, with great reduction in electric resistance as a whole, as will be obvious from a comparison with the similar characteristics of the conventional humidity sensor that does not employ the material of the invention and that is shown in a dotted line in FIG. 2.

Figure 6:
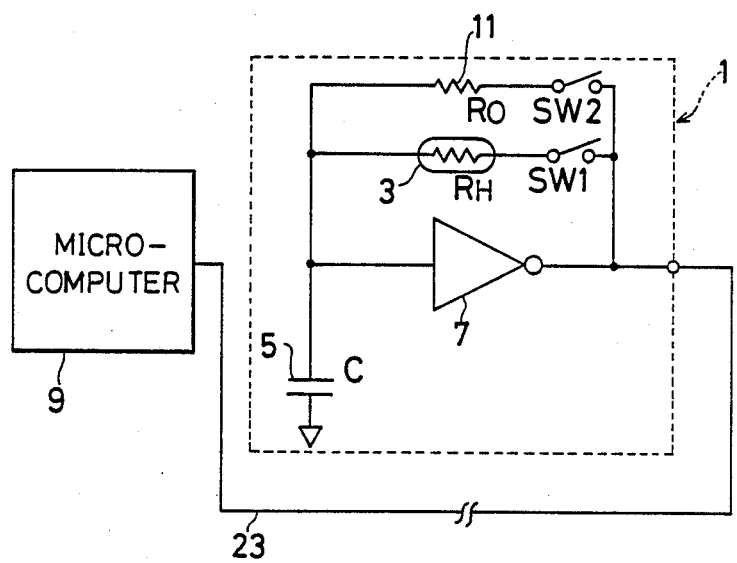
FIG. 6 is a circuit diagram of a third embodiment of the electronic hygrometer of the invention.

FIG. 6 illustrates an electronic hygrometer as a third embodiment of the invention. As can be seen from FIG. 6, the third embodiment comprises the square-wave pulse generator 1 of the electronic hygrometer shown in FIG. 1 installed in a space where measurement is to be taken away from the point where the microcomputer 9 is installed. The square-wave pulse generator 1 is connected to the microcomputer 9 via a signal transmission line, i.e., a cable 23 of a given length, so that the humidity can be detected in the measuring space.

Figure 7:
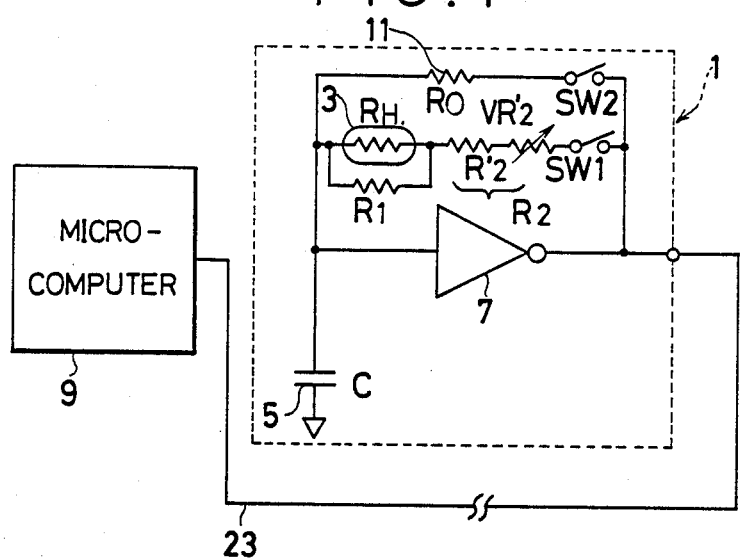
FIG. 7 is a circuit diagram of a fourth embodiment of the electronic hygrometer of the invention.

FIG. 7 illustrates an electronic hygrometer as a fourth embodiment of the invention. Like the third embodiment, this embodiment comprises the square-wave pulse generator 1 of the electronic hygrometer shown in FIG. 3 and the microcomputer 9 connected together by a cable 23. The electronic hygrometers of the afore-described structures were contrived under the circumstances to be described below. The conventional electronic hygrometer comprises the square-wave pulse generator 1 and the microcomputer 9 as a unitary structure to constitute an integral measuring instrument. Meanwhile, automatic air-conditioning control systems are in use for remote, centralized control away from the spaces being air-conditioned, such as greenhouses where vegetables and fruits are cultivated, places for manufacturing special articles that require strict humidity control, warehouses, office buildings, and other residential buildings. In such cases, the above-mentioned systems pose a problem of inconvenience in that the measuring instrument must be carried by the operator to the spot where the humidity is to be measured and the data must be reported back to the original point. In order to solve the problem in accordance with the invention, the square-wave pulse generator 1 is made separate from the microcomputer 9 and connected to the latter by the cable 23.

Figure 8:
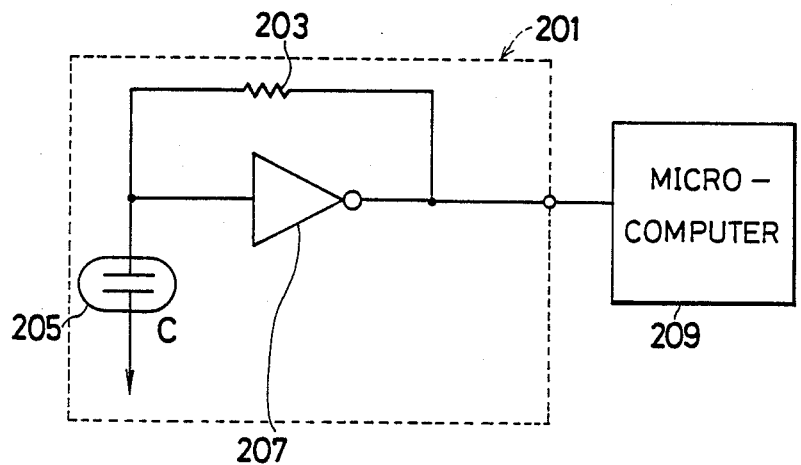
FIG. 8 is a circuit diagram of a fifth embodiment of the electronic hygrometer of the invention.
Figure 9:
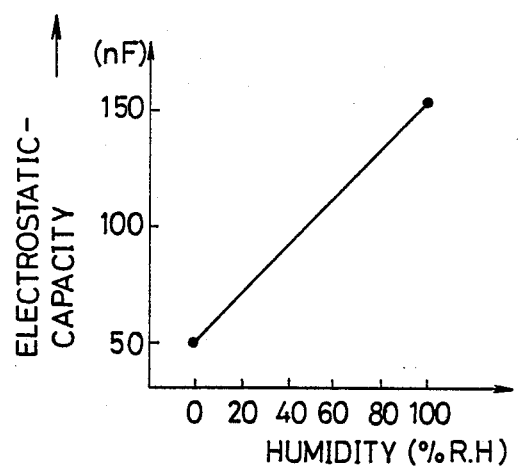
FIG. 9 is a graph showing the humidity-electrostatic capacity characteristics of the humidity sensor used in the electronic hygrometer of FIG. 8.
Figure 10:
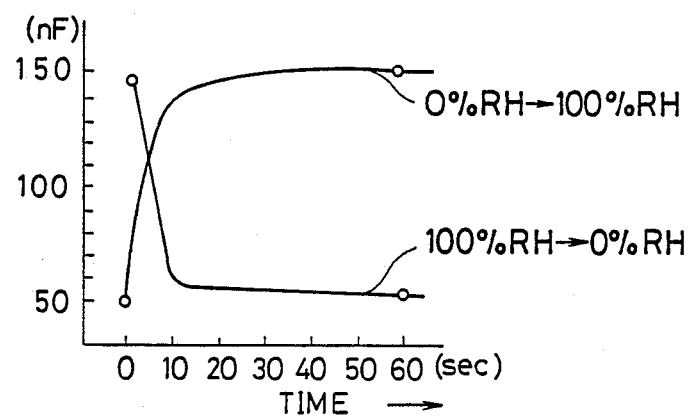
FIG. 10 is a graph showing the moisture absorption-desorption response characteristics of the humidity sensor used in the electronic hygrometer of FIG. 8.

FIG. 8 illustrates an electronic hygrometer as a fifth embodiment of the invention. As will be obvious from FIG. 8, the fifth embodiment comprises a square-wave pulse generator 201 and a microcomputer 209 which receives output signals from the generator 201. The square-wave pulse generator 201 is constituted by the same inverter element 207 as used in the first to fourth embodiments, a resistance element 203 constituting the feedback circuit of the inverter element 207, and a humidity sensor 205 which forms a CR time-constant circuit or a CR oscillation circuit with the electric resistance of the resistance element 203. The humidity sensor 205 uses a humidity sensing element of a so-called electrostatic capacity variable type, in which the electrostatic capacity varies with the humidity change of the atmosphere. The humidity sensing element of the type may consist of an anode substrate composed of a valve-action metal such as tantalum, titanium, niobium, aluminum, or hafnium partly anodized to form a dielectric anodized film thereon, a thermally decomposable metal salt such as manganese nitrate thermally decomposed to form a semiconductor metal oxide layer such as of manganese dioxide on the whole or part of the dielectric anodized film, and a water vapor-permeable, electrically conductive electrode of carbon or silver paint formed on the top. The humidity sensing element of the type detects the humidity in the following way. As the humidity sensor 205 absorbs water from the air in an amount corresponding to the relative humidity, the absorbed water acts as an electrode opposite to the dielectric anodized film. When the humidity is high, the area of the electrode increases and a large electrostatic capacity is obtained. When the humidity is low, a small electrostatic capacity is detected as a signal and the change in relative humidity of the air is finally detected as a change in the electrostatic capacity. The humidity sensor of the electrostatic capacity variable type exhibits high measurement accuracy and sensitivity over a range of 0 to 100% RH as shown in FIG. 9 and further shows very great moisture absorption-desorption response characteristics as shown in FIG. 10. The data stored in the memory of the microcomputer 209 and the details of processing performed by the microcomputer 290 are the same as those described in connection with the foregoing embodiments and are not described here.

Figure 11:
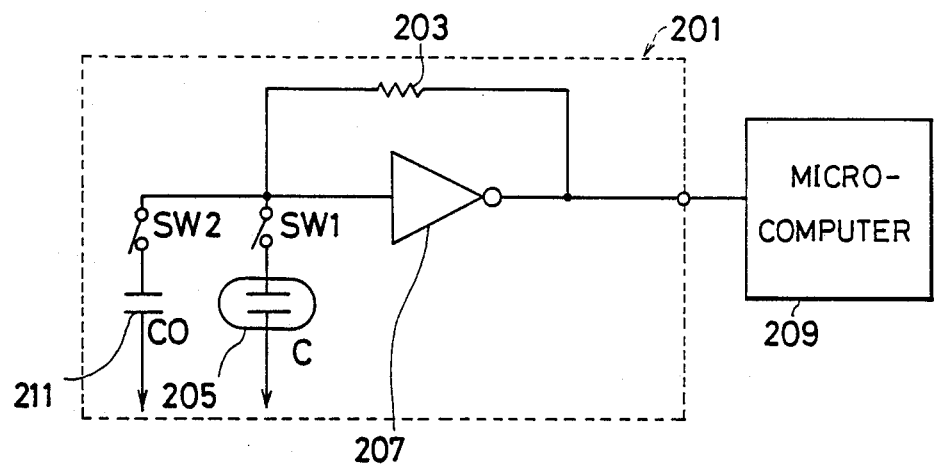
FIG. 11 is a circuit diagram of a sixth embodiment of the electronic hygrometer of the invention.

FIG. 11 shows an electronic hygrometer as a sixth embodiment of the invention. Referring to FIG. 11, a reference capacity element CO211 is connected in parallel with a humidity sensor 205 connected to the input of the inverter element 207 of the square-wave pulse generator 201 shown in FIG. 8. A switch SW1 which opens and closes the circuit connected to the humidity sensor 205 and a switch SW2 which opens and closes the circuit connected to the reference capacity element CO211 are provided. The microcomputer 209 calculates the ratio $rf=fH/fO$ of an oscillation frequency fH of square-wave pulse signals output from the square-wave pulse generator 201 when the switch SW1 only is closed to an oscillation frequency fO of square-wave pulse signals from the square-wave pulse generator 201 when the switch SW2 only is closed, the ratio rf corresponding to the ratio $CO/C$ of the electrostatic capacity C of the humidity sensor 205 to the electrostatic capacity CO of the reference capacity element CO211. From the relationship $rf=fH/fO=CO/C$, the microcomputer 9 then finds the value C, assuming that $C=CO/rf$, whereby the humidity of the atmosphere is found from the value C and the data given in FIG. 9. The square-wave pulse generator 201 is constructed as described above for the following reasons. Our experiments with the square-wave pulse generator 201 of FIG. 8 revealed that the oscillation frequency f of the generator 201 is influenced to some extent by variations in the resistance R of the resistance element 203, high-level threshold voltage VTH of the inverter element 207, low-level threshold voltage VTL of the inverter element 207, output voltage VO of the generator 201, and constant K, and also by their temperature characteristics. We therefore connected the reference resistance element CO211 in parallel with the humidity sensor 205 and provided the switches SW1 and SW2 in such a manner that when one was closed the other was open. The oscillation frequency fH $$\left( fH = 1 / \left\{ k \cdot R \cdot C \cdot \ln \frac{VO - VTL}{VO - VTH} \right\} \right)$$

when the switch SW1 only was closed and the oscillation frequency fO $$\left( fO = 1 / \left\{ k \cdot R \cdot CO \cdot \ln \frac{VO - VTL}{VO - VTH} \right\} \right)$$

when the switch SW2 only was closed, were counted by the microcomputer 209. Then, the ratio of fH to fO were found to erase VTH, VTL, VO, k, and C, and the oscillation frequency f was determined from the value CO/C only, whereby more accurate data of humidity measurement than before were obtained. The changes in electrostatic capacity of the reference capacity element CO211 with changes in temperature are almost negligible as compared with the changes in such other characteristics as VTH, VTL, VO, R, and k. By finding the ratio rf=fH/fO, therefore, the values VTH, VTL, VO, R, and k can be cancelled. The ratio rf is determined solely by the electrostatic capacity of the humidity sensor 205. In this way humidity is measured with high precision. Ordinary analog switches or three-state buffers are used as the switches SW1 and SW2.

Figure 12:
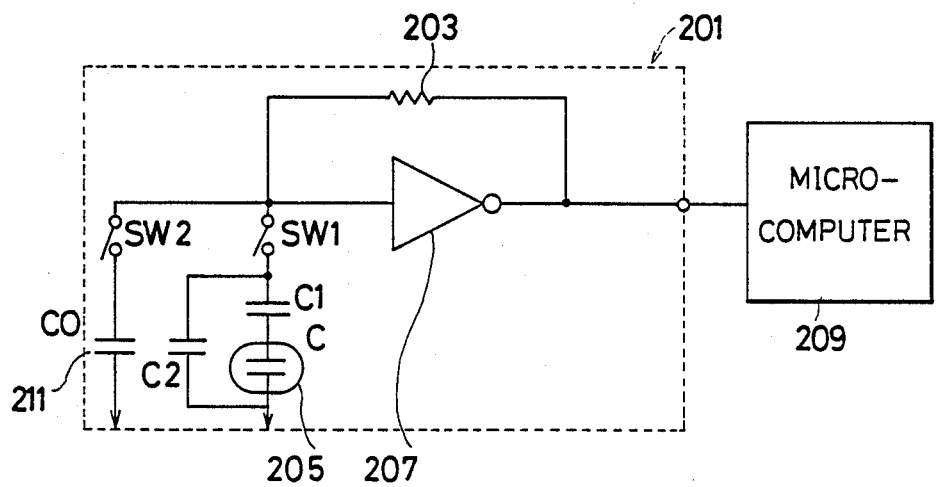
FIG. 12 is a circuit diagram of a seventh embodiment of the electronic hygrometer of the invention.

FIG. 12 illustrates an electronic hygrometer as a seventh embodiment of the invention. As shown in FIG. 12, the electronic hygrometer comprises the square-wave pulse generator 201 having the circuit structure shown in FIG. 11, wherein a capacitor C1 having an electrostatic capacity C1 greater than that C of the humidity sensor 205 in the steady state is connected in series with the element 205 which, in turn, is connected to the input of the inverter element 207, to form a resultant capacity C' together with the electrostatic capacity C of the humidity sensor 205, and a capacitor C2 having an electrostatic capacity C2 smaller than that C of the humidity sensor 205 in the steady state is connected in parallel with the resultant capacity C'

$$\left( = \frac{1}{\frac{1}{C} + \frac{1}{C1}} \right)$$

formed by the humidity sensor 205 and the capacitor C1 connected in series, in order to form a resultant capacity C''(=C'+C2). The upper limit of resultant capacity C'' of the humidity sensor 205 and capacitors C1 and C2 is restricted to be less than the sum C1+C2 of the electrostatic capacities of the capacitors C1 and C2, and the lower limit of the resultant capacity C'' is restricted to be not smaller than the electrostatic capacity C2 of the capacitor C2. The square-wave pulse genertor 201 is constructed as above because of the reasons explained below. The electrostatic capacity C of the humidity sensor 205 that varies with the change in humidity of the atmosphere is limited so as not to exceed or fall below a predetermined value, so that the square-wave pulse generator 201 will not send to the microcomputer 209 any square-wave pulse signal of a frequency higher or lower than the oscillation frequency data in a given range stored in the memory of the microcomputer 209. If a square-wve pulse signal of a frequency outside the present oscillation frequency range is output from the square-wave pulse generator 201, the CPU instructs the display unit (not shown) to indicate the overflow or underflow. In this embodiment, the variation of electrostatic capacity C of the humidity sensor 205 is confined within a predetermined range. For this purpose, the capacitor C1 having the electrostatic capacity C1 greater than that C of the humidity sensor 205 in the steady state is connected in series with the sensor 205, and the capacitor C2 having the electrostatic capacity C2 smaller than that C of the humidity sensor 205 is connected in parallel with the sensor 205 and the capacitor C1 that are connected in series, so that the resultant capacity C' of the humidity sensor 205 and the capacitor C1 connected in series will not become greater than the electrostatic capacity C1 of the capacitor C1. The resultant capacity C'' of the humidity sensor 205 and capacitors C1 and C2 is limited to be C''<C'+C2 when the electrostatic capacity C of the humidity sensor 205 increases, and is limited to be C''>C2 when the electrostatic capacity C decreases and the resultant capacity C' becomes very small.

Figure 13:
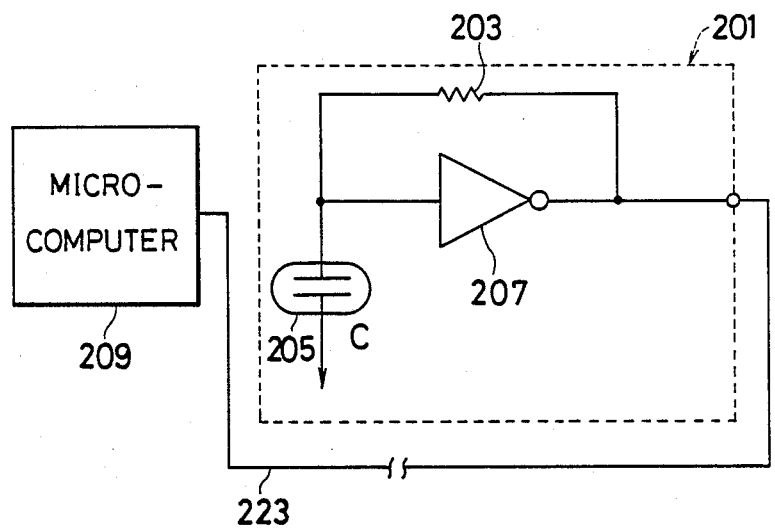
FIG. 13 is a circuit diagram of an eighth embodiment of the electronic hygrometer of the invention.
Figure 14:
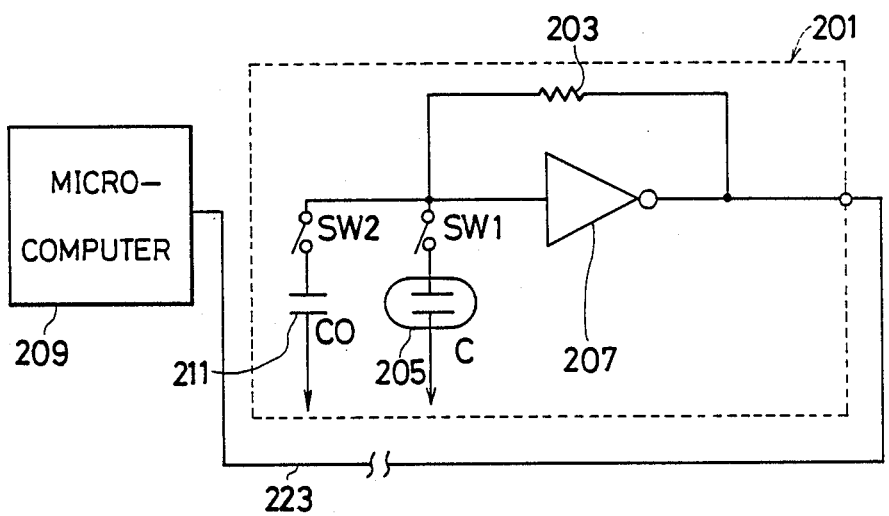
FIG. 14 is a circuit diagram of a ninth embodiment of the electronic hygrometer of the invention.

FIG. 13 illustrates an electronic hygrometer as an eighth embodiment of the invention. As will be obvious from FIG. 13, the electronic hygrometer consists of the square-wave pulse generator 201 of the electronic hygrometer of FIG. 8 that is installed in a desired space where measurement is to be taken remote from the point where the microcomputer 209 is installed the square-wave pulse generator 201 being connected to the microcomputer 209 by a cable 223 of a given length so that the humidity can be detected at the site of measurement.

Figure 15:
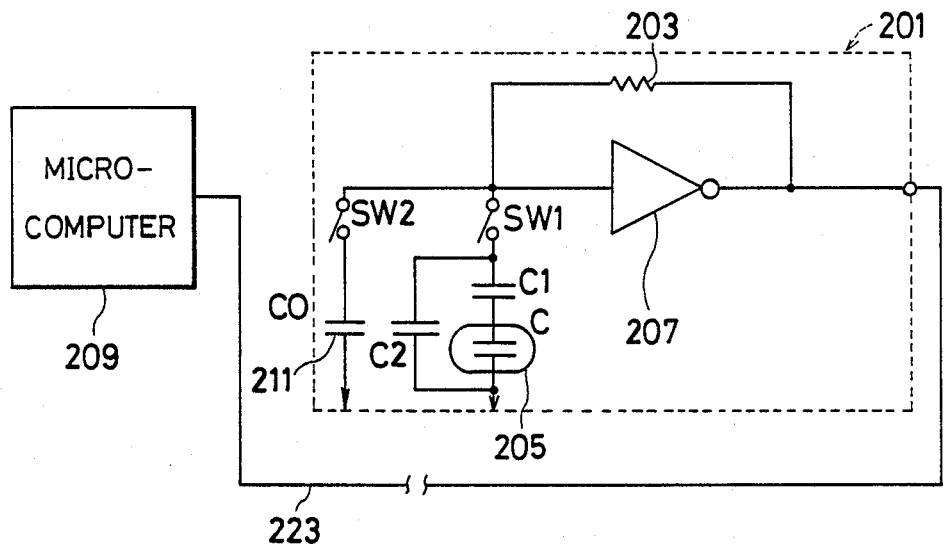
FIG. 15 is a circuit diagram of a tenth embodiment of the electronic hygrometer of the invention.

FIG. 4 shows an electronic hygrometer as a ninth embodiment of the invention and FIG. 15, a tenth embodiment. The ninth embodiment consists of the square-wave pulse generator 201 of the electronic hygrometer shown in FIG. 11 that is connected to the microcomputer 209 by a cable 223. Similarly, the tenth embodiment consists of the square-wave pulse generator 201 of the electronic hygrometer of FIG. 12 that is connected to the microcomputer 209 by a cable 223. The circumstances under which the electronic hygrometers as the eighth to tenth embodiments of the invention were contrived are the same as those for the third and fourth embodiments, and are not described here again.

Figure 16:
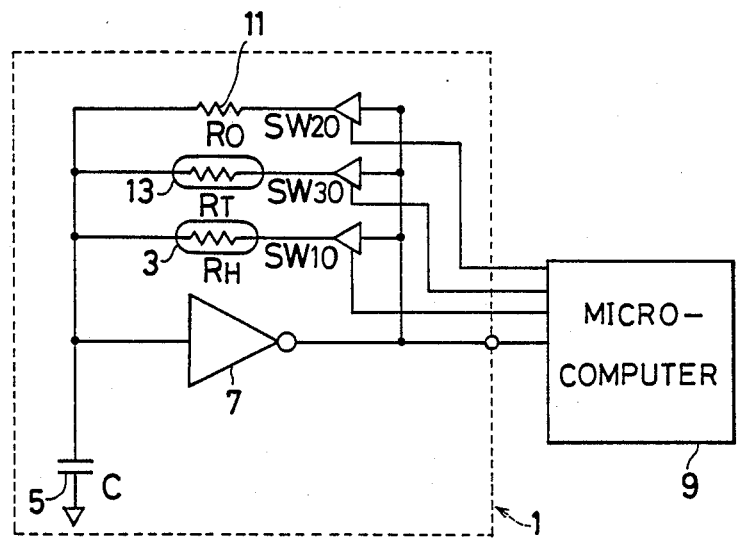
FIG. 16 is a circuit diagram of an electronic thermohydrometer as an eleventh embodiment of the invention.
Figure 17:
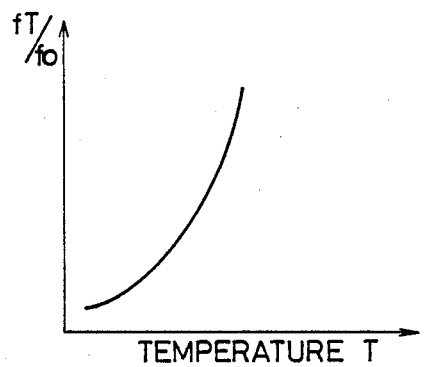
FIG. 17 is a graph showing the temperature-fT/fO characteristics of the temperature sensor used in the electronic thermohygrometer of FIG. 16.

FIG. 16 illustrates an electronic thermohygrometer as an eleventh embodiment of the invention. As is clear from FIG. 16, the electronic thermohygrometer consists of the square-wave pulse generator 1 of the circuit structure shown in FIG. 1, wherein a temperature sensor 13 such as a thermistor whose electric resistance is variable with the temperature change of the atmosphere is connected in parallel with the ceramic humidity sensing element 3 inserted in the feedback circuit of the inverter element 7 and with the reference resistance element RO11 connected in parallel with the humidity sensing element 3, and a third switching means SW30 is provided to open and close the circuit of the temperature sensor 13. The microcomputer 9 calculates a ratio rf=fH/fO of an oscillation frequency fH of square-wave pulse signals output from the square-wave pulse generator 1 when the first switching means SW10 only is closed to an oscillation frequency fO of square-wave pulse signals from the generator 1 when the second switching means SW20 only is closed, the ratio rf corresponding to a ratio RO/RH of the electric resistance RH of the ceramic humidity sensing element 3 to the resistance RO of the reference resistance element RO11. The microcomputer 9 further calculates a ratio r'f=fT/fO of an oscillation frequency fT of square-wave pulse signals output from the square=wave pulse signal generator 1 when the switching means SW30 only is closed to an oscillation frequency fO of square-wave pulse signals from the generator 1 when the switching means SW20 only is closed, the ratio r'f corresponding to a ratio RO/RT of the electric resistance RT of the temperature sensor 13 to the resistance RO of the reference resistance element RO11. From the relationship rf=fH/fO=RO/RH, the value RH is found on the basis of RH=RO/rf, and the humidity of the atmosphere is found from the value RH and the data represented by the solid lines in FIG. 2. The temperature of the atmosphere is also found from the value r'f=fT/fO and the data of temperature-fT/fO characteristics shown in FIG. 17 and stored in the memory of the microcomputer 9. The circuit structure of the square-wave pulse generator 1 of the electronic thermohygrometer as the eleventh embodiment of the invention was constructed as described above for the reasons now to be explained. It was found in detecting the temperature the oscillation frequency of the square-wave pulse generator 1 is influenced to some extent by variations in C, k, VTH, VTL, and VO and by the temperature characteristics as in detecting the humidity in the manner described in conjunction with the first embodiment. As stated, the influences of VTH, VTL, VO, k, and C are removed by utilizing the relationship between the value fT/fO and the temperature. This embodiment uses three-state buffers for the switches SW10, SW20, and SW30.

Figure 18:
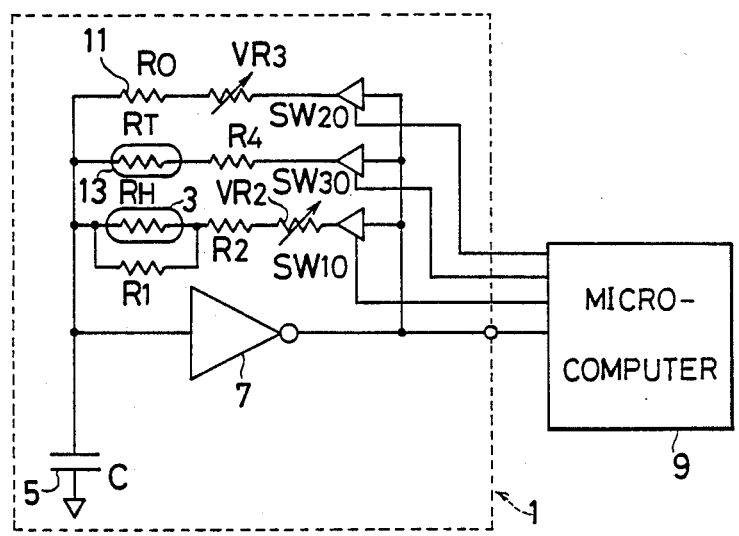
FIG. 18 is a circuit diagram of an electronic thermohydrometer as a twelfth embodiment of the invention.

FIG. 18 illustrates an electronic thermohygrometer as a twelfth embodiment of the invention. Referring to FIG. 18, the electronic thermohygrometer consists of the square-wave pulse generator 1 of the circuit structure shown in FIG. 16, wherein a first protective resistance element, or protective resistance element R1, is connected in parallel with the ceramic humidity sensing element 3 inserted in the feedback circuit of the inverter element 7. A second protective resistance element, or fixed resistance element R2, and a variable resistance element VR2 connected in series, are connected together in series with a resultant resistance of the humidity sensing element 3 and the protective resistance element R1 that are connected in parallel. A third protective resistance element, or variable resistance element VR3, is connected in series with the reference resistance element RO11 connected in parallel with the ceramic humidity sensing element 3. A fourth protective resistance element, or protective resistance element R4, is connected in series with a temperature sensor 13 that is connected in parallel with the humidity sensing element 3 and with the reference resistance element RO11. As explained in conjunction with the second embodiment, the construction keeps the frequency of signals output from the square-wave pulse generator 1 from deviating out of the specified range of the oscillation frequency data by controlling the electric resistances of the ceramic humidity sensing element 3 and the temperature sensor 13 that vary with changes in humidity and temperature of the atmosphere, lest the resistances exceed or fall below a predetermined range. Also, the variable resistance element VR2 is adjusted correspondingly to the adjustment of the variable resistance element VR3, lest the accuracy of humidity measurement by the humidity sensing element 3 be not adversely affected by the adjustment of the element VR3 which may be resorted to in order to compensate for any variation in resistance of the temperature sensor 13, e.g., due to the common use of the reference resistance element RO11 by the humidity sensing element 3 and by the temperature sensor 13.

Figure 19:
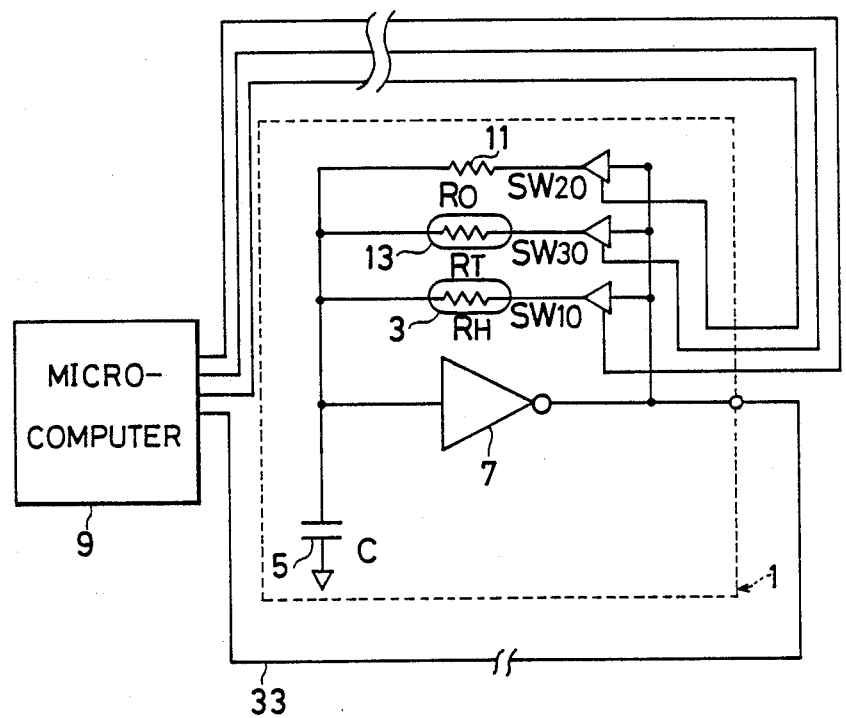
FIG. 19 is a circuit diagram of an electronic thermohygrometer as a thirteenth embodiment of the invention.
Figure 20:
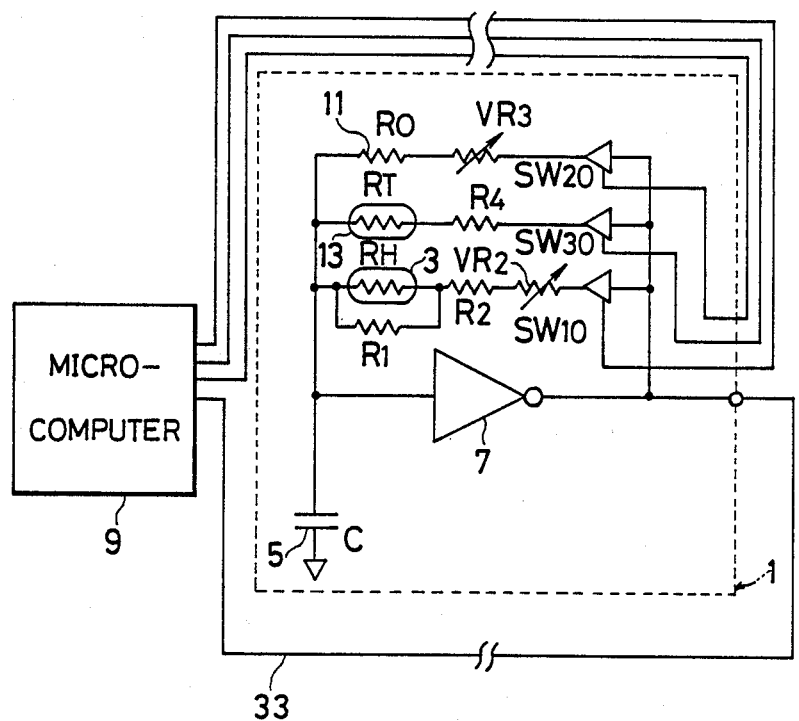
FIG. 20 is a circuit diagram of an electronic thermohydrometer as a fourteenth embodiment of the invention.

FIG. 19 illustrates an electronic thermohygrometer as a thirteenth embodiment of the invention. As will be obvious from FIG. 19, the electronic thermohygrometer has the square-wave pulse generator 1 of the electronic thermohygrometer of FIG. 16 that is installed in a desired space remote from the point where the microcomputer 9 is installed, the square-wave pulse generator 1 being connected to the microcomputer 9 by a cable 33 of a given length so that the humidity can be detected in the desired space for measurement. FIG. 20 shows an electronic thermohygrometer as a fourteenth embodiment of the invention. Like the thirteenth embodiment, this electronic thermohygrometer has the square-wave pulse generator 1 of the electronic thermohygrometer of FIG. 18 that is connected to the microcomputer 9 by a cable 33. The circumstances in which the thirteenth and fourteenth embodiments were contrived are the same as those for the third and fourth embodiments and are not explained here.

In the eleventh to fourteenth embodiments of the invention, the humidity sensor used an element of the so-called electric resistance variable type whose electric resistance varies with the humidity change of the atmosphere. This is not a limitation to the electronic thermohygrometer of the invention, however. For example, the humidity sensor may, of course, use instead an element of the so-called electrostatic capacity variable type whose electrostatic capacity varies with the humidity change of the atmosphere.

According to this invention, as described above, the frequency of square-wave pulse signals output from the oscillation means is counted, and the humidity of the atmosphere is determined on the basis of the count. The relatively expensive a-d converter can be eliminated and the number of circuit components decreased. Consequently, the whole circuit can be built up in a single-chip LSI, and thus an electronic hygrometer is provided which features reduced size, power consumption, and cost. Moreover, calculation is made to find the ratio of an oscillation frequency of square-wave pulse signals output from the oscillation means when the first switching means only is closed to an oscillation frequency of square-wave pulse signals from the oscillation means when the second switching means only is closed, the ratio corresponding to the ratio of the electric resistance of the humidity sensor to the resistance of the reference resistance element. Calculation is also made to find the ratio of an oscillation frequency of square-wave pulse signals output from the oscillation means when the third switching element only is closed to an oscillation frequency of square-wave pulse signals output from the oscillation means when the second switching means only is closed, the ratio corresponding to the ratio of the electric resistance of the temperature sensor to the resistance of the reference resistance element. The humidity of temperature of the atmosphere is then determined on the basis of the calculated result. This makes it possible to eliminate the relatively expensive a-d converter and decrease the number of circuit components. Therefore, the whole circuit can be contained in a single-chip LSI, realizing an electronic thermohygrometer small in size with reduced power consumption and manufacturing cost.

What is claimed is:

1. An electronic thermohygrometer comprising: oscillation means which includes a square-wave pulse signal generator, a humidity sensor connected in parallel with the square-wave pulse signal generator for constituting a first feedback circuit of the square-wave pulse signal generator and which exhibits electric resistance variable with the humidity change of the atmosphere, a reference resistance element connected in parallel with the humidity sensor for constituting a second feedback circuit of the square-wave pulse signal generator, a temperature sensor connected in parallel with the humidity sensor and the reference resistance element for constituting a third feedback circuit of the square-wave pulse signal generator and which exhibits electric resistance variable with the temperature change of the atmosphere, first selectably operable switching means for opening and closing the first feedback circuit with the humidity sensor, second selectably operable switching means for opening and closing the second feedback circuit with the reference resistance element, third selectably operable switching means for opening and closing the third feedback circuit with the temperature sensor, and a capacity element connected between the input of the square-wave pulse signal generator and a reference voltage and which forms a CR time constant circuit with a selectable one of the electric resistance of the humidity sensor, the electric resistance of the reference resistance element, and the electric resistance of the temperature sensor, said oscillation means producing square-wave pulse signals corresponding to changes in electric resistance of the humidity sensor when the first switching means only is closed, producing square-wave pulse signals corresponding to the resistance of the reference resistance element when the second switching means only is closed, and producing square-wave pulse signals corresponding to changes in electric resistance of the temperature sensor when the third switching means only is closed; and digital operation processing means for calculating (1) the ratio of the oscillation frequency of square-wave pulse signals output from the oscillation means when the first switching means only is closed to the oscillation frequency of square-wave pulse signals from the oscillation means when the second switching element only is closed, said ratio corresponding to the ratio of the electric resistance of the humidity sensor to the resistance of the reference resistance element, and (2) the ratio of the oscillation frequency of square-wave pulse signals output from the oscillation means when the third switching means only is closed to the oscillation frequency of square-wave pulse signals from the oscillation means when the second switching means only is closed, said ratio corresponding to the ratio of the electric resistance of the temperature sensor to the resistance of the reference resistance element, and for determining (3) the humidity and the temperature of the atmosphere on the basis of the calculated ratios.

2. An electronic thermohygrometer according to claim 1, wherein said humidity sensor is a ceramic humidity sensing element made of zirconia ($ZrO_2$) which contains at least one selected from yttria ($Y_2O_3$), calcia (CaO), and magnesia (MgO) in the form of a solid solution.

3. An electronic thermohygrometer according to claim 1 or 2, wherein said oscillation means has a signal transmission line of a predetermined length which connects the same to said digital operation processing means, so that the humidity is detected in a space where the measurement is to be taken remote from said digital operation processing means.

* * * * *